US008465435B2

(12) United States Patent
Van Goudoever et al.

(10) Patent No.: US 8,465,435 B2
(45) Date of Patent: Jun. 18, 2013

(54) METHOD, A SYSTEM AND A COMPUTER PROGRAM PRODUCT FOR DETERMINING A BEAT-TO-BEAT STROKE VOLUME AND/OR A CARDIAC OUTPUT

(75) Inventors: Jeroen Van Goudoever, Amstelveen (NL); Olaf Schraa, Amsterdam (NL); Karel H. Wesseling, The Hague (NL)

(73) Assignee: Bmeye B.V., Amsterdam (NL)

( * ) Notice: Subject to any disclaimer, the term of this patent is extended or adjusted under 35 U.S.C. 154(b) by 456 days.

(21) Appl. No.: 12/669,890

(22) PCT Filed: Jul. 20, 2007

(86) PCT No.: PCT/NL2007/050362
§ 371 (c)(1),
(2), (4) Date: Apr. 29, 2010

(87) PCT Pub. No.: WO2009/014420
PCT Pub. Date: Jan. 29, 2009

(65) Prior Publication Data
US 2010/0217134 A1 Aug. 26, 2010

(51) Int. Cl.
*A61B 5/02* (2006.01)
(52) U.S. Cl.
USPC .................................... 600/485; 600/526
(58) Field of Classification Search
USPC ................................. 600/485, 526
See application file for complete search history.

(56) References Cited

U.S. PATENT DOCUMENTS 5,400,793 A 3/1995 Wesseling
6,315,735 B1 * 11/2001 Joeken et al. ............... 600/500
6,461,305 B1 10/2002 Schnall
2003/0135124 A1 7/2003 Russell
2006/0235323 A1 10/2006 Hatib et al.

OTHER PUBLICATIONS

Written Opinion of the International Searching Authority, International application No. PCT/NL2007/050362.
Wesseling K H et al: "Computation of aortic flow from pressure in humans using a nonlinear, three-element model" Journal of Applied Physiology, American Physiological Society, US, vol. 74, No. 5, 1993, pp. 2566-2573, XP008072952 ISSN: 8750-7587.
Papaioannou Theodoros G et al: "Experimental and clinical study of the combined effect of arterial stiffness and heart rate on pulse pressure: differences between central and peripheral arteries" Clinical and Experimental Pharmacology and Physiology, vol. 32, No. 3, Mar. 2005, pp. 210-217, XP002475189 ISSN: 0305-1870.

* cited by examiner

*Primary Examiner* — Navin Natnithithadha
*Assistant Examiner* — Etsub Berhanu
(74) *Attorney, Agent, or Firm* — Michael Crapenhoft

(57) ABSTRACT

The invention relates to a method 10 for determining a beat-to-beat stroke volume 9a and/or a cardiac output 9b based on a measurement 2 of suitable arterial pressure data. At the step 4 a waveform of the arterial pressure pulse is assessed based on data obtained during the measurement of step 2. At step 6 a compliance or impedance in dependence of at least one measurement of arterial pressure data is computed using a non-linear model 7. The non-linear model may comprise an arctangent model. The arctangent model may be differentiated numerically or analytically to obtain the compliance or the impedance of an aortic portion. The thus obtained compliance or impedance may then be substituted into a linear model 8. The linear model 8 may comprise a Windkessel model 8a, or a Waterhammer model 8b or any other suitable linear pulse contour model 8c. As a result, the beat-to-beat stroke volume 9a and/or cardiac output 9b are computed.

10 Claims, 4 Drawing Sheets

Figure 1:
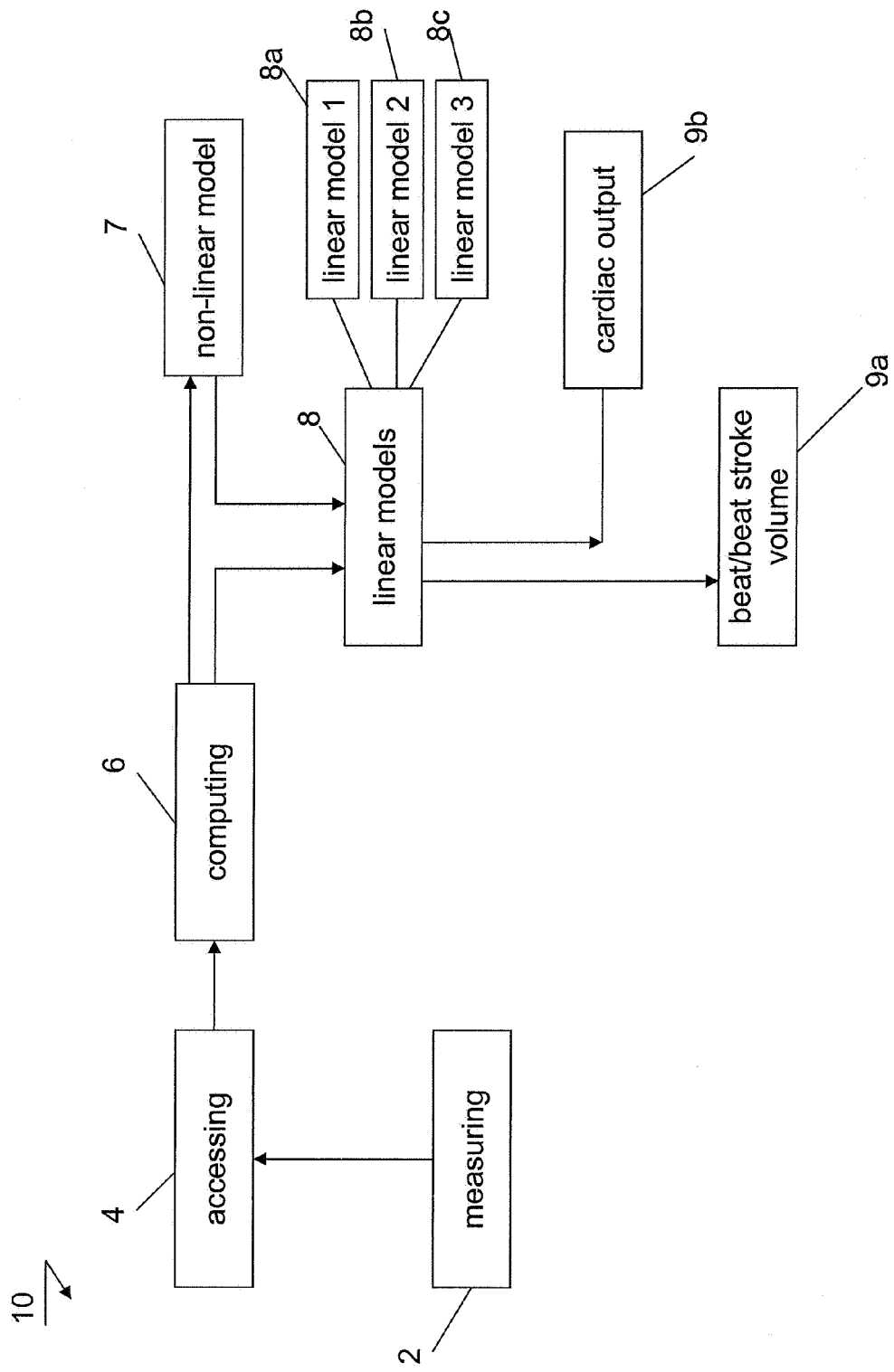

ID, A SYSTEM AND A COMPUTER PROGRAM PRODUCT FOR DETERMINING A BEAT-TO-BEAT STROKE VOLUME AND/OR A CARDIAC OUTPUT

FIELD OF THE INVENTION

The invention relates to a method for determining a beat-to-beat stroke volume and/or a cardiac output based on at least one measurement of an arterial pressure data.

The invention further relates to a computer program product for determining a beat-to-beat stroke volume and/or a cardiac output based on at least one measurement of an arterial pressure data.

The invention still further relates to a system for determining a beat-to-beat stroke volume and/or a cardiac output based on at least one measurement of an arterial pressure data.

BACKGROUND OF THE INVENTION

Blood pressure and cardiac output, or pressure and flow, respectively, in the aorta of a patient, define its hemodynamic state. This hemodynamic state may change on a short time scale of seconds and minutes requiring continuous or semi-continuous monitoring. Thus, instrumentation has been developed for over a century for measuring both blood pressure and flow on a continuous basis. Unfortunately, the measurement of cardiac output (i.e. flow) is almost impossible to perform in a safe and continuous way. In contrast, blood pressure can be measured in patients on a continuous basis by invasive means with a little risk, but not entirely without risk, and more recently also non-invasively with the per se known Finapres methodology. Hence, there is a need for a method to derive flow from pressure using a computation instead of a measurement.

When recording pulsatile blood pressure and flow simultaneously in experimental animals, it was observed that if flow went up so did blood pressure and when flow went down blood pressure went down. Both hemodynamic signals are thus coupled. From physics and engineering one knows that pressure and flow are related via an impedance: $p=qZ$, with $p$ pressure, $q$ flow, and $Z$ impedance. The proper impedance to relate aortic flow to aortic pressure is referred to as aortic impedance. But it is hard if not impossible to determine the aortic impedance in an individual patient. In principle, the impedance can be derived from the pressure and flow as $$Z=p/q,$$

but the flow (q) cannot be measured easily as a waveform. A possible approach is the use of suitable models.

Windkessel Model

The oldest model for the hemodynamic properties of the aorta is the so-called "Windkessel" model. The equation to compute a stroke volume from the contour of the pressure pulse according to the Windkessel model is as follows:

$$Vs=C(p2-p1)(1+As/Ad)$$

with Vs—a stroke volume, C—an aortic compliance defined as dV/dP, p2—a pressure at a dicrotic notch, p1 the diastolic pressure, As the integrated area under the systolic portion of the blood pressure curve, and Ad similarly the diastolic area. The dicrotic notch is a pulse that precedes a dicrotic wave, it being a pulse sequence comprising a double-beat sequence wherein a second beat is weaker than a first beat. It is a disadvantage of this model that the compliance C of the aorta must be known. In practice the compliance is an unknown variable. In the prior art, the compliance has been determined indirectly by calibrating this value. To this purpose, a cardiac output has been measured with a standard clinical technique such as Fick or indicator dilution, Qi. A stroke volume from an indicator dilution, Vsi, follows as Vsi=Qi/f, with f being the heart rate. The compliance C now follows as the ratio C=Vsi/Vs (C=1). Once calibrated, the method can be used to follow changes and trends in stroke volume, for monitoring purposes.

However, this method has been shown to be unreliable. Various studies have been performed in which the compliance has been calibrated, followed by administrating of a vasoactive drug to change blood pressure, heart rate and cardiac output. It appeared that the compliance C changed with the drugs given, in various directions. This yielded that the Windkessel method might not be useful in practice.

Uniform Tube or Waterhammer Model

Another hemodynamic model of the aorta is the uniform tube with characteristic impedance, or Zc model. It describes the relation between pulsatile p(t) pressure and pulsatile flow q(t) in a uniform tube, while ignoring any mean pressure component:

$$q(t)=p(t)/Zc$$

with q(t) the pulsatile flow waveform, p(t) pulsatile pressure, and Zc the aortic characteristic impedance. Integrating the pulsatile signals from diastolic pressure, pd, during systole (when blood is ejected from the heart) one obtains:

$$Vs=1/Zc\int(p(t)-pd)dt$$

In this equation, the impedance Zc is unknown and can only be determined with an individual patient by calibration with a clinical cardiac output method, as described above for the Windkessel method. When tested under the same circumstances as the Windkessel method, described above, Waterhammer method also appeared unreliable although to a lesser degree, since Zc can be written as:

$$Zc=\sqrt{(r/)(AC')}$$

with r the density of blood, A the aortic cross-sectional area and C' the compliance per unit length. When A increases, C' decreases rendering their product and thus impedance Zc relatively constant.

SUMMARY OF THE INVENTION

It is an object of the invention to provide a reliable method for determining a beat-to-beat stroke volume and/or a cardiac output based on at least one measurement of an arterial pressure data.

To this end a method according to the invention comprises the steps of:
  computing a compliance or impedance in dependence of at least one measurement of arterial pressure data using a non-linear model;
  using said compliance or impedance in a pulse contour method for determining the beat-to-beat stroke volume and/or cardiac output based on the measured arterial pressure data.

It is noted that the cardiac output equals the stroke volume multiplied by a heart beat frequency. A method according to the invention can be based on the insight that a per se known linear pulse contour method, like Windkessel or Waterhammer method, can be improved if respective values of pressure dependence of compliance and impedance that are obtained from a suitable non-linear model are incorporated in these linear models. A suitable example of a non-linear model is the per se known aortic arctangent model.

The Aortic Arctangent Model

The aortic mechanical properties of post mortem segments of the thoracic aorta of humans have been measured in vitro over the entire physiological pressure range. The responses of the internal cross-sectional area of the aorta to an increase in pressure could be fitted closely by an arctangent:

$$A(p) = Am(0.5 + (1/\pi) \arctan((p-p0)/p1)) \qquad (1)$$

in which:
A is the cross-sectional area in $cm^2$;
Am is the maximal area at very high pressure;
p0 indicates the inflexion point of a pressure curve;
p1 indicates a halfwidth of a pressure pulse.

For implementing a method of the invention for the arterial pressure data a pressure waveform may preferably be selected.

In addition, a method according to the invention can be based on further insights and assumptions:

1/ the total aortic mechanical properties can be described by the multiplication of the thoracic segment area by an "effective length" Le:

$$V(p) = A(p)Le \qquad (2)$$

with V(p) the pressure dependent volume of the aorta. It is assumed that properties of the thoracic aorta are representative for the entire length of the aorta. This assumption is advantageous as it simplifies the model to a great extent. Preferably, the effective length of the aorta is about 0.5 a height of the person. Due to this assumption a further simplification of the model can be obtained.

2/ the parameters Am, p0 and p1 of the arctangent model are linearly dependent on gender and age of the patient. It has been empirically proven that this assumption substantially holds for p0, and is reasonably correct for p1. Thus, given the two well known properties of a patient—gender and age, the individual physiological scatter in the aortic parameters p0 and p1 can be reduced substantially. In order to improve accuracy in approximating the maximal area Am at very high pressure, a one time calibration may be necessary. This improves computation accuracy for determining the stroke volume and/or the cardiac output even further.

3/ a viscous component of the aortic mechanical properties is ignored. A corresponding pure elastic compliance then follows from differentiating the equation for the pressure-dependent cross-sectional area A(p) with respect to pressure, yielding:

$$C(p) = Cm/(1 + ((p-p0)/p1)^2) \qquad (3)$$

with $$Cm = Am/(\pi p1),$$

wherein
C(p) is a pressure-dependent compliance;
Cm—is a maximum compliance of the aortic portion.

The above equations (1)-(3) for cross-sectional area, volume and compliance of the aorta (and thus also for characteristic impedance) are applicable to any of the known pulse contour models yielding an improved method for determining the beat-to-beat stroke volume and/or the cardiac output based on at least one measurement of an arterial pressure data, notably the waveform. The operation of a method according to the invention and further advantageous embodiments thereof will be discussed with reference to FIG. 1. Further advantageous embodiments of a method according to the invention are set forth in the claims.

The computer program product according to the invention comprises instructions for causing a processor to carry out the steps of a method as is set forth in the foregoing. The operation of the computer program will be discussed in more detail with reference to FIG. 2.

A system according to the invention comprises:
a processing unit arranged for:
 computing a compliance or impedance in dependence of at least one measurement of arterial pressure data using a non-linear model;
 using said compliance or impedance in a pulse contour method for determining a beat-to-beat stroke volume and/or cardiac output based on the measured arterial pressure data.

The operation of a system according to the invention will be discussed in more detail with reference to FIG. 3. FIG. 4 presents a preferred embodiment of a non-invasive measurement sensor arrangement for use in a system of FIG. 3.

These and other aspects of the invention will be discussed in more detail with reference to the figures.

BRIEF DESCRIPTION

FIG. 1 presents a schematic view of an embodiment of a method according to the invention.

Figure 2:
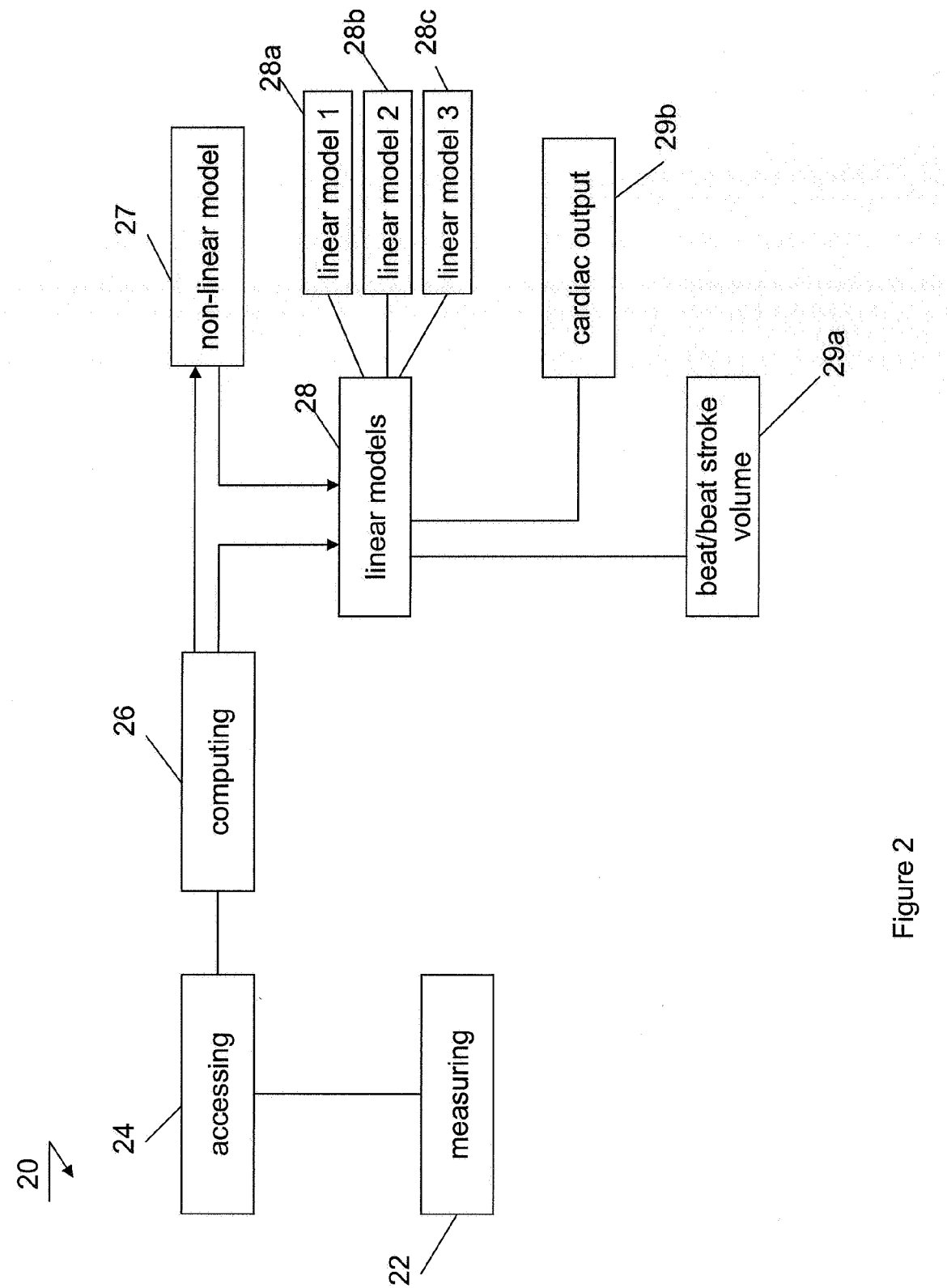

FIG. 2 presents in a schematic way an embodiment of a flow-chart of a computer program according to the invention.

Figure 3:
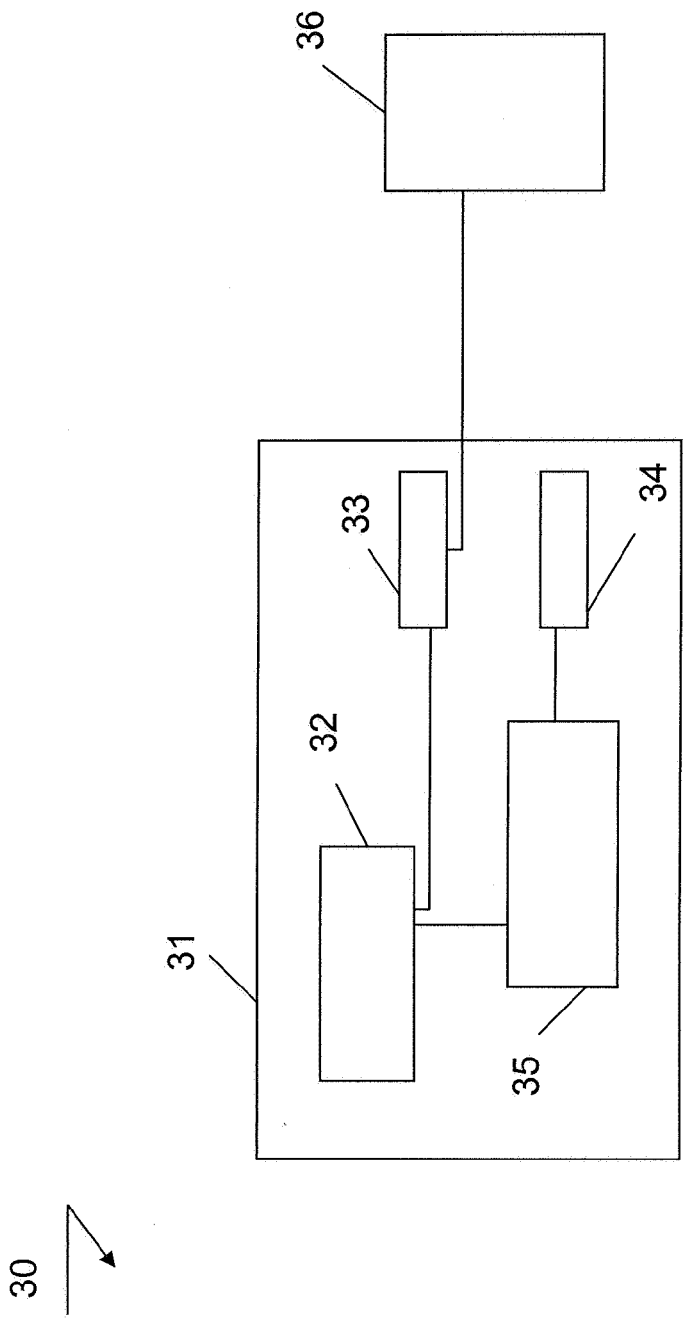
Figure 4:
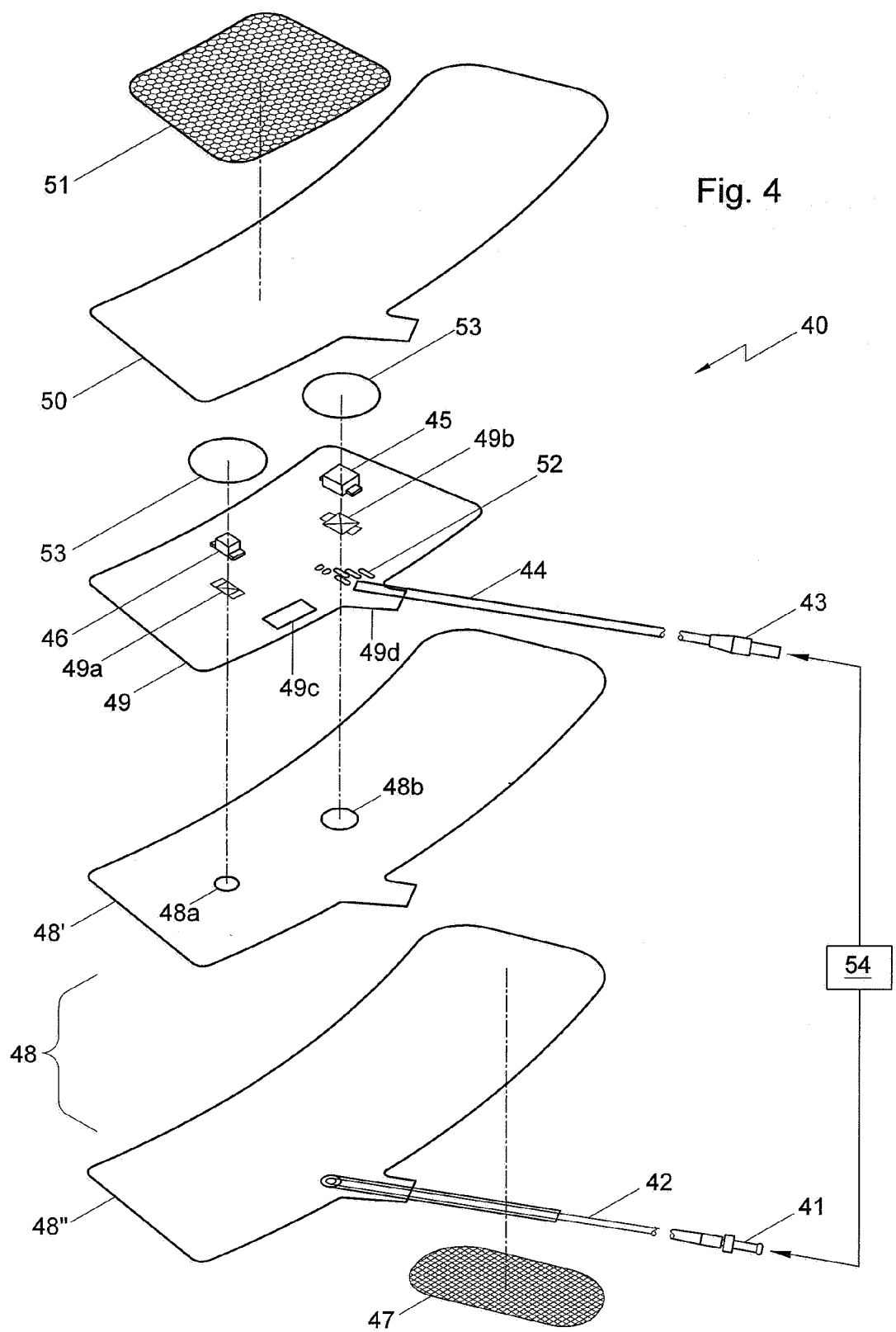

FIG. 3 presents a schematic view of an embodiment of a system according to the invention.

FIG. 4 presents a schematic view of an embodiment of a cuff for use in a system of FIG. 3.

It is noted that common parts are identified with common reference numerals. It is further noted that figures and description thereof are illustrative, not limiting, whereas a combination of details discussed with reference to different figures is contemplated as well. FIG. 1 presents a schematic view of an embodiment of a method according to the invention. A method 10 according to the invention is arranged for determining a beat-to-beat stroke volume 9a and/or a cardiac output 9b based on a measurement 2 of suitable arterial pressure data, notably an arterial pressure waveform. It is noted that for purposes of said measurement any per se known suitable invasive or non-invasive system may be used. Preferably, a system as is discussed with reference to FIG. 3 or FIG. 4 is used. At the step 4 a waveform of the arterial pressure pulse is assessed based on data obtained during the measurement of step 2. At step 6 a compliance or impedance in dependence of at least one measurement of arterial pressure data is computed using a non-linear model. Preferably, equation (1) as is discussed above may be used for said computation, which may be accessed at step 7 of the method 10. The non-linear model may comprise an arctangent model. The arctangent model may be differentiated numerically or analytically to obtain the compliance or the impedance of an aortic portion. The thus obtained compliance or impedance may then be substituted into a linear model 8. The linear model 8 may comprise a Windkessel model 8a, or a Waterhammer model 8b or any other suitable linear pulse contour model 8c.

It is noted that the aortic arctangent model has never been earlier incorporated into a linear pulse contour model. Moreover, there have been no suggestions that an improvement of a calculation of a stroke volume and/or a cardiac output can be reached if the arctangent module were incorporated therein.

It is found to be advantageous to calculate the beat-to-beat stroke volume or the cardiac output based on a total effective aortic compliance. The total aortic compliance may be described by a beat-to-beat compliance per unit length of the aorta and an effective length of the aorta dependent on the person-specific characteristic. Preferably, a height of the person is selected for the person-specific characteristic, the effective length of the aorta being given by preferably Le=0.5*H, wherein H is height of the person. More preferably, a heart rate dependent model is included in a computational model. This may be achieved by computing the aortic compliance for an effective pressure. Preferably, a mean pressure during systole is selected, which may be calculated based on a beat-to-beat pressure for a contraction frequency of the heart. Due to incorporation of the heart rate dependent model into computation of the beat-to-beat stroke volume or the cardiac output, a further improvement of computational accuracy is achieved.

When the non-linear model (1) is applied to the Windkessel model one obtains:

$$Vs = C(p)(p2-p3)(1+As/Ad), \text{ wherein}$$

Vs is a stroke volume;
C(p) is an aortic compliance;
p2 is a pressure at a dicrotic notch;
p3 is a diastolic pressure,
As is an integrated area under a systolic portion of a blood pressure curve;
Ad is an integrated area under a diastolic portion of a blood pressure curve.

It is found that a major improvement in the reliability of the Windkessel method may be achieved if the compliance C(p) is assumed constant for each beat and it's value is obtained from the equation (3) for C(p) at a fixed, so-called "effective" pressure level, pe, for that beat. Hence, the C is replaced by a C(pe), with pe to be determined from the measured arterial pressure data.

Due to the fact that the cross-sectional area of the aorta is being approximated by the non-linear model, an improvement of the computation accuracy for determining the beat-to-beat stroke volume and/or the cardiac output is obtained. In particular, it is found to be advantageous to approximate a pressure dependent volume V(p) of the aorta by the product of the cross-sectional area of the aorta and the effective length Le of the aorta, the corresponding equation being given by:

$$V(p) = A(p)Le,$$

wherein the cross-sectional area of the aorta A(p) may be approximated by the arctangent model, given by the equation (1). Due to this estimation a simple and reliable equation for the computation of the pressure-dependent arterial volume is obtained.

When the non-linear model (1) is applied to the Waterhammer model, one obtains:

$$Z(w, pe) = Z_0 + RZc/(R+Zc)$$

wherein
Z is an total impedance of the aortic portion;
$Z_0$ is an characteristic impedance of the aorta;
Zc is 1/jwC;
w=2πf, with f the heart rate in Hz;
R is a resistance;
C is an aortic compliance, for example approximated by a non-linear model.

It is found to be advantageous to iteratively determine the resistance R. The resistance may also be referred to as a systemic vascular resistance. This can be performed in accordance with a following algorithm. First, the stroke volume is computed for R=1. From the resultant stroke volume a cardiac output is obtained by multiplication by a heart rate. Second, R is computed from the mean pressure divided by cardiac output. Third, the entire stroke volume computation is repeated again and again with the recently obtained R until consecutive values differ by less than 1% or reaches a maximum number of iterations. Preferably, several iterations are carried out, for example five. By iteratively adjusting a value of the resistor R an improvement of the computation accuracy is further obtained.

FIG. 2 presents in a schematic way an embodiment of a flow-chart of the computer program according to the invention. The computer program 20 according to the invention is arranged for determining beat-to-beat stroke volume and/or cardiac output based on at least one measurement of an arterial pressure waveform. The computer program 20 may be stored as an executable file in a suitable memory of a computer. Alternatively, the computer program 20 may comprise a suitable number of executable subroutines which are called in sequence during the execution of the method as is discussed with reference to FIG. 1. The computer program may be stored on a suitable carrier, like a disk. The computer program 20 may also be integrated in a measuring system arranged for determining an arterial pressure data, for example a waveform, and for processing the thus obtained data. In this case the computer program may comprise an instruction 22 for causing a suitable interface for collecting raw data, notably from an invasive or a non-invasive device. A suitable example of a computer-controlled non-invasive sensor is an inflatable cuff, discussed with reference to FIG. 4. Upon an event the measuring data is collected, the computer program 20 follows to an instruction 24 for processing said data. As a result the arterial waveform is accessed. After this, an instruction 26 is initiated causing a suitable processor to calculate compliance or an impedance of an aortic portion from a non-linear model. A suitable non-linear model may be accessed using instruction 27. The non-linear model 27 may comprise the arctangent model, which may de differentiated for obtaining the impedance or the compliance of the aorta. Upon an event, this calculation is taken place, the compliance or impedance data may be fed into a per se known linear model, using the instruction 28. Suitable linear models, like Waterhammer 28a or Windkessel model 28b have been discussed with reference to the method of the invention. Finally, the computer program comprises instructions 29a, 29b for determining beat-to-beat volume and/or cardiac output based on the compliance or impedance data and said pulse contour model. It is possible that the beat-to-beat-stroke volume or cardiac output are computed based on different linear models and the respective results are averaged or suitably weighted.

FIG. 3 presents a schematic view of an embodiment of the system according to the invention. The system 30 comprises a processor 31 and a measurement unit 36, which may be arranged either to perform invasive or non-invasive measurements of the arterial pressure data, notably a waveform. Data collected by the measurement unit are provided to the input 33 of the processor 31. The processor 31 may further comprise storage means 32 for storing a suitable non-linear model for computing a compliance or impedance in dependence of at least one measurement of arterial pressure data. The processor 31 may further comprise a computing unit 35 for using said compliance or impedance in a pulse contour method for determining the beat-to-beat stroke volume and/or cardiac output based on the measured arterial pressure data. The storage means 32 may be arranged to store the per se known pulse contour models, like Waterhammer model and/or Windkessel model. Preferably, the computing means is arranged to use an arctangent model for said non-linear model. In this way a system is provided for determining beat-to-beat stroke volume and/or cardiac output based on the measurement of an arterial pressure waveform with increased accuracy compared to prior art.

FIG. 4 presents a schematic view of an embodiment of a cuff for use in the system of FIG. 3. The cuff 40 comprises a photoplethysmograph arranged with an emitter of suitable radiation 46 and a detector of the radiation 45. In addition the cuff 40 comprises an inflatable bladder 48 provided with an air supply channel 42 for inflating the bladder and for evacuating it. The cuff 40 is conceived to be arranged on a portion of the body, for example about a finger of a person, whereby a signal related to a blood flow in said portion is acquired using the photoplethysmograph. During the data acquisition the inflatable bladder in pressurized so that an external pressure is applied to the portion being investigated. For this purpose the air supply channel 42 may comprise a suitable fitting 41 for connecting to a pump, notably a gas pump.

Photoplethysmographs are known per se. An operational principle of the photoplethysmograph is based on the fact that with each cardiac cycle the heart pumps blood to the periphery of the body. A change in volume of the arteries or arterioles caused by the pressure pulse of the systolic wave is detected by illuminating the skin with a suitable light, notably emitted from a Light Emitting Diode (LED) and then measuring the amount of light either transmitted or reflected to a suitable detector, notably a photodiode. Alternatively, the emitter 46 may be arranged to emit infrared radiation. Still alternatively, the photoplethysmograph may be arranged in a transmissive set-up wherein the detector 45 is arranged to measure a portion of radiation transmitted trough a tissue of the patient. In case of a reflective set-up a portion of the radiation reflected from the tissue is detected. Each cardiac cycle appears as a peak in a signal from the photoplethysmograph. The shape of a signal waveform from the photoplethysmograph differs from subject to subject, and varies with a location and a manner in which the cuff is attached to the tissue. It is noted that the photoplethysmograph can be attached to a great plurality of areas on the human body, for example on a finger, on an ear, in a nostril, on the temples of the head. The photoplethysmograph may even be arranged in a body cavity.

In the embodiment shown, the inflatable bladder 48 comprises a top-layer 48" conceived to be brought in contact with a portion of a body of a person, notably with a finger, and a back-layer 48' which may be attached to a flexible printed circuit 49. It is noted that the back-layer is preferably directly attached to the flexible printed circuit 49 without using any additional adhesive inter-layers. The top-layer 48" is arranged to be more flexible than the back-layer 48'. Due to this substantially only the top-layer of the inflatable bladder undergoes deformation in use, due to pressure within said bladder. Because a deformation of the back-layer 48' might influence an emitter—detector geometry, it is advantageous to provide the inflatable bladder wherein substantially only the top-layer undergoes deformation in use. Due to this feature an increase in measurement accuracy is achieved. The back-layer 48' may be attached to the top-layer 48" by any suitable technique, preferably a sealing method is used.

The inflatable bladder 48 may further comprise cut-away areas 48a and 48b, wherein the emitter 46, notably a light emitting device (LED) and a detector 45, notably a photodiode are positioned, respectively. The flexible printed circuit 49 may comprise corresponding cut-away areas 49a, 49b for accommodating the emitter 46 and the detector 45. The flexible printed circuit 49 may further comprise suitable blockers 53 for shielding the emitter 46 and the detector 45 from interference with other light sources or detectors. Preferably, the detector 45 is also shielded from ambient light. Preferably, the blockers 53 comprise an opaque flexible material. A signal from the light detector 45 is picked up by suitable electronic components (not shown) of the flexible printed circuit 49. The flexible printed circuit 49 is electrically connectable to the cable 44 provided with a suitable electric connector 43. It is possible that the cable 44 and the air supply 42 are housed in a joint housing having sole outside connector 54. Preferably, the flexible printed circuit 49 further comprises a module 49c for processing the signal from the detector 45. Suitable signal processing steps may comprise, but are not limited to, filtering, amplification, and/or the like.

The cuff 40 may further comprise a sticker 50. A loop 51 and hook 47 may be arranged to fasten the cuff about a finger of a person. Preferably, the top-layer 48" is manufactured from a biocompatible material and extends substantially over the same length as the back layer 48' or label 50. Due to this the label or back layer does not have to be manufactured from a biocompatible material reducing the production costs of the cuff. The top-layer manufactured from a biocompatible material may enhance possibility of a durable monitoring using the cuff, without causing irritation to a tissue of the person.

Preferably, a surface of the flexible printed circuit conceived to face the tissue in use comprises an electrically conductive coating, preferably an electrically conductive and optically opaque and reflective coating. In accordance with this technical measure radiation impinging the coating will be reflected back towards the tissue. In addition, a proper electrical shielding of the flexible printed circuit may be enabled. The opacity of the flexible circuit material advantageously prevents the detector of the photoplethysmograph from interference of ambient light with the photoplethysmograph. It is noted that a usually envisaged protective layer for covering metallic traces of the flexible printed circuit can be left out on the inner surface of the flexible printed circuit, which further reduces manufacturing costs of the cuff. Metal traces, notably copper traces, may be used in the flexible printed circuit to connect the electrical cable 44 to the components of the flexible printed circuit, which makes wiring redundant, further decreasing manufacturing costs of the cuff according to the invention. The flexible printed circuit may be shaped with a tail-end 49d for relieving fastening strain to the wiring and the air tube in use.

While specific embodiments have been described above, it will be appreciated that the invention may be practiced otherwise than as described. The descriptions above are intended to be illustrative, not limiting. Thus, it will be apparent to one skilled in the art that modifications may be made to the invention as described in the foregoing without departing from the scope of the claims set out below.

What is claimed is:

1. A method for determining a beat-to-beat stroke volume or a cardiac output based on at least one measurement of arterial pressure data, the method comprising the steps of:

obtaining at least one measurement of arterial pressure data using a measurement unit;

providing the at least one measurement of arterial pressure data to a processor; and causing the processor to perform the steps of:

computing a compliance or impedance in dependence of at least one measurement of arterial pressure data using a non-linear model, said non-linear model being given by the following equation:

$$A(p)=Am(0.5+(1/\pi)\arctan((p-p0)/p1)),$$

wherein $A(p)$ is the pressure-dependent cross-sectional area of the aorta in $cm^2$, Am is the maximal area of the aorta at very high pressure;

p0 is a parameter indicating an inflection point of a pressure curve A(p); and p1 is a parameter describing a half-width of the pressure curve;

using said compliance or impedance in a pulse contour method for determining the beat-to-beat stroke volume or cardiac output based on the measured arterial pressure data;

approximating parameters of the non-linear model based on a further model based on a person-specific characteristic;

using the approximated parameters for the non-linear model; and computing the aortic compliance for an effective pressure, wherein for the effective pressure a mean pressure during systole is selected that is computed beat-to-beat for a contraction frequency of the heart.

2. A method according to claim 1, wherein for the arterial pressure data an arterial pressure waveform is selected.

3. A method according to claim 2, wherein said non-linear model is conceived to approximate a pressure dependency of a cross-sectional area of a portion of aorta.

4. A method according to claim 1, wherein the non-linear model is used to approximate mechanical properties of the total aorta.

5. A method according to claim 4, wherein the mechanical property is a pressure dependent volume V(p) of the aorta, the pressure dependent volume V(p) of the aorta being approximated by an equation of:

$$V(p)=A(p)Le,$$

wherein Le is an effective length of the aorta.

6. A method according to claim 5, wherein the effective length of the aorta is taken to be about 0.5 a height of the person.

7. A method according to claim 1, wherein a compliance per unit length is derived from the non-linear model, and wherein a total effective aortic compliance is calculated by the processor by taking into account the compliance per unit length in combination with an effective length of the aorta dependent on the person-specific characteristics.

8. A method according to claim 1, wherein for the pulse contour method a Waterhammer model is used, given by an equation of:

$$Z(w, pe)=Z_0+R\,Zc/(R+Zc)$$

wherein:

Z is a total impedance of the aortic portion;

$Z_0$ is a characteristic impedance of the aorta;

Zc is $1/jwC$;

$w=2\pi f$, with f the heart rate in Hz;

R is a resistance;

pe is an effective pressure level for the beat; and

C is an aortic compliance.

9. A method according to claim 8, further comprising the step of causing the processor to determine a value of the resistance R iteratively.

10. A method according to claim 9, wherein iterations comprise:

determining a stroke volume for an initial value of the resistance R;

determining a cardiac output from the stroke volume;

determining a further value for the resistance based on a means pressure and a cardiac output;

repeating a new stroke volume computation using the further value of the resistance; and updating the value for the resistance R based on a new value of the stroke volume.

* * * * *